United States Patent
Shin et al.

(10) Patent No.: US 11,064,906 B2
(45) Date of Patent: Jul. 20, 2021

(54) METHOD AND APPARATUS FOR DETERMINING RESPIRATION STATE BASED ON PLURALITY OF BIOLOGICAL INDICATORS CALCULATED USING BIO-SIGNALS

(71) Applicant: ELECTRONICS AND TELECOMMUNICATIONS RESEARCH INSTITUTE, Daejeon (KR)

(72) Inventors: Hyun Soon Shin, Sejong-si (KR); Do Hyung Kang, Seoul (KR); Chan Young Hahm, Daejeon (KR); Seung Yoon Nam, Busan (KR); John Lorenzo, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 313 days.

(21) Appl. No.: 16/260,364

(22) Filed: Jan. 29, 2019

(65) Prior Publication Data
US 2019/0231221 A1    Aug. 1, 2019

(30) Foreign Application Priority Data

Jan. 29, 2018 (KR) ........................ 10-2018-0010982
Nov. 28, 2018 (KR) ........................ 10-2018-0149342

(51) Int. Cl.
*A61B 5/08* (2006.01)
*A61B 5/0531* (2021.01)
(Continued)

(52) U.S. Cl.
CPC .......... *A61B 5/0816* (2013.01); *A61B 5/0531* (2013.01); *A61B 5/0533* (2013.01);
(Continued)

(58) Field of Classification Search
CPC ............ A61B 5/08–0816; A61B 5/085; A61B 5/0205; A61B 5/0531–0533; A61B 5/02416
See application file for complete search history.

(56) References Cited

U.S. PATENT DOCUMENTS 6,091,973 A * 7/2000 Colla .................. A61B 5/0205
                                                         600/324
10,004,427 B1 * 6/2018 Shoeb .................. A61B 5/7221
(Continued)

FOREIGN PATENT DOCUMENTS

JP    2016-126500 A    7/2016
KR   10-2012-0029361 A   3/2012
(Continued)

*Primary Examiner* — Thaddeus B Cox
(74) *Attorney, Agent, or Firm* — LRK Patent Law Firm

(57) ABSTRACT

A method and apparatus for determining a respiration state on the basis of a plurality of biological indicators calculated using bio-signals. The method for determining a respiration state on the basis of a plurality of biological indicators calculated using bio-signals includes collecting a photoplethysmography (PPG) signal measured by a PPG sensor and a cutaneous electric signal measured by an electrodermal activity (EDA) sensor; analyzing the collected PPG signal and cutaneous electric signal and calculating a plurality of biological indicators including a respiration rate; and comprehensively evaluating the plurality of biological indicators to determine a user's respiration state.

16 Claims, 7 Drawing Sheets

(51) Int. Cl.
    *A61B 5/0533*   (2021.01)
    *A61B 5/024*    (2006.01)
    *A61B 5/00*     (2006.01)
    *A61B 5/16*         (2006.01)
    *A61B 5/113*        (2006.01)

(52) U.S. Cl.
    CPC ............ *A61B 5/0806* (2013.01); *A61B 5/725* (2013.01); *A61B 5/7278* (2013.01); *A61B 5/02416* (2013.01); *A61B 5/113* (2013.01); *A61B 5/165* (2013.01); *A61B 5/681* (2013.01); *A61B 5/6898* (2013.01); *A61B 5/7203* (2013.01); *A61B 5/7207* (2013.01); *A61B 5/7225* (2013.01)

(56) References Cited

U.S. PATENT DOCUMENTS

| | | | |
|---|---|---|---|
| 2010/0145171 A1 | 6/2010 | Park et al. | |
| 2011/0313260 A1 | 12/2011 | Jeong et al. | |
| 2012/0130201 A1* | 5/2012 | Jain | A61B 5/08 600/301 |
| 2012/0302900 A1* | 11/2012 | Yin | A61B 5/0816 600/484 |
| 2013/0060098 A1* | 3/2013 | Thomsen | A61B 5/14551 600/301 |
| 2016/0206212 A1* | 7/2016 | Lee | A61B 5/6801 |
| 2017/0245808 A1* | 8/2017 | Jain | A61B 5/746 |
| 2017/0325740 A1* | 11/2017 | Barnes | A61B 5/0205 |
| 2018/0035910 A1 | 2/2018 | Conchell Ano | |
| 2019/0167176 A1* | 6/2019 | Annoni | A61B 5/0205 |

FOREIGN PATENT DOCUMENTS

| | | |
|---|---|---|
| KR | 10-1601895 B1 | 3/2016 |
| KR | 10-1669878 B1 | 10/2016 |
| KR | 10-2017-0113252 A | 10/2017 |
| KR | 10-2017-0136727 A | 12/2017 |

* cited by examiner

METHOD AND APPARATUS FOR DETERMINING RESPIRATION STATE BASED ON PLURALITY OF BIOLOGICAL INDICATORS CALCULATED USING BIO-SIGNALS

CROSS REFERENCE TO RELATED APPLICATIONS

This application claims priority to Korean Patent Application No. 10-2018-0010982, filed Jan. 29, 2018, and No. 10-2018-0149342, filed Nov. 28, 2018, in the Korean Intellectual Property Office (KIPO), the entire contents of which are hereby incorporated by reference.

BACKGROUND

1. Field of the Invention

Example embodiments of the present invention relate in general to a method and apparatus for determining a respiration state based on a plurality of biological indicators calculated using bio-signals, and more particularly, to a technique for calculating a respiration rate and an oxygen saturation from a photoplethysmography (PPG) signal, calculating a cutaneous electric conductivity from an electrodermal activity (EDA) signal, and then synthesizing the calculated plurality of biological indicators to determine a respiration state.

2. Description of Related Art

One important factor in determining the health status of panic disorder patients, anxiety disorder patients, congenital heart disease neonates, intensive care unit patients, and elderly people is a respiration state.

By observing a respiration state, it is possible to quickly detect a change in a subject's heath state. In this case, an urgent respiration state may be determined when the subject has airway obstruction (suffocation), a disease (or pneumonia), a respiratory disorder (emphysema or asthma), an electric shock, a shock, a water accident, a heart attack, a heart disease, a damage to chest or lung, allergies (food or insect bites), a drug, addictions (toxic inhalation or ingestion), or the like.

Therefore, it is necessary to accurately and promptly detect and cope with dyspnea, which is the most common phenomenon in respiratory emergencies, in daily life or in medical institutions.

Recently, along with the wide use of wearable devices such as smart bands and pads, and mobile terminals using wireless communication, studies for sensing a respiration state using such devices are increasing.

However, most existing methods have low accuracy and applicability because an apparatus that is difficult to easily monitor in daily life should be used or because a respiration state is determined just using a respiration rate as an indicator.

Accordingly, there is a need for a method capable of precisely and promptly determining a respiration state by synthesizing various bio-signals that may appear in a subject.

SUMMARY

Accordingly, example embodiments of the present invention are provided to substantially obviate one or more problems due to limitations and disadvantages of the related art.

Example embodiments of the present invention provide a method of determining a respiration state on the basis of a plurality of biological indicators calculated using bio-signals.

Example embodiments of the present invention also provide an apparatus for determining a respiration state on the basis of a plurality of biological indicators calculated using bio-signals.

Example embodiments of the present invention also provide a method of calculating the number of breaths per minute using bio-signals.

In some example embodiments, there is provided a method of determining a respiration state on the basis of a plurality of biological indicators calculated using bio-signals.

The method of determining a respiration state on the basis of a plurality of biological indicators calculated using bio-signals may include collecting a photoplethysmography (PPG) signal measured by a PPG sensor and a cutaneous electric signal measured by an electrodermal activity (EDA) sensor, analyzing the collected PPG signal and cutaneous electric signal and calculating a plurality of biological indicators including a respiration rate, and comprehensively evaluating the plurality of biological indicators to determine a user's respiration state.

The calculating of the plurality of biological indicators may include performing bandpass filtering on the PPG signal to extract a respiration signal and performing frequency analysis on the extracted respiration signal on a segment basis to calculate a respiration rate.

The performing of the frequency analysis to calculate the respiration rate may include determining an optimal size of sample data shared by continuous segments.

When the number of samples is N and the size of each segment is $\alpha \cdot N$, the optimal size ($\beta \cdot N$) of sample data may be determined to satisfy a relationship corresponding to the following equation:

$$\alpha \cdot N + x \cdot y = N$$

where, $y = (\alpha \cdot N) - (\beta \cdot \alpha \cdot N)$ $$x = 1/\alpha \cdot ((1-\alpha))/((1-\beta))$$

The plurality of biological indicators may further include a blood oxygen saturation and a cutaneous electric conductivity.

The PPG signal may be a signal that is acquired from reflected light with wavelengths of 660 nm and 940 nm.

The calculating of the plurality of biological indicators may include normalizing a 660-nm wavelength signal and a 940-nm wavelength signal of the PPG signal at a ratio of an alternating current signal to a direct current signal and calculating the blood oxygen saturation using a ratio between the normalized 660-nm wavelength signal and the normalized 940-nm wavelength signal.

The calculating of the blood oxygen saturation may include calculating the blood oxygen saturation to have a linear proportional relationship at the ratio between the normalized 660-nm wavelength signal and the normalized 940-nm wavelength signal.

The determining of the user's respiration state may include determining the respiration state as "normal respiration state" when the respiration rate falls within a normal threshold range, the blood oxygen saturation is greater than a minimal critical oxygen saturation, and the cutaneous electric conductivity is less than a neutral critical cutaneous conductivity.

The determining of the user's respiration state may include determining the respiration state as "abnormal physical or psychological state" when the respiration rate falls within a normal threshold range and the blood oxygen saturation is less than a minimal critical oxygen saturation or the cutaneous electric conductivity is greater than a neutral critical cutaneous conductivity.

The determining of the user's respiration state may include determining the respiration state as "dyspnea accompanied by oxygen deficiency symptoms due to hyperpnea" when the respiration rate is greater than a maximum value of a normal threshold range and the blood oxygen saturation is less than a minimal critical oxygen saturation.

The determining of the user's respiration state may include determining the respiration state as "dyspnea accompanied by a sticky skin symptom due to hyperpnea" when the respiration rate is greater than a maximum value of a normal threshold range and the cutaneous electric conductivity is greater than a neutral critical cutaneous conductivity.

The determining of the user's respiration state may include determining the respiration state as "urgent respiration state" when the respiration rate lies outside a normal threshold range, the blood oxygen saturation is less than a minimal critical oxygen saturation, and the cutaneous electric conductivity is greater than a neutral critical cutaneous conductivity.

In other example embodiments, there is provided an apparatus for determining a respiration state on the basis of a plurality of biological indicators calculated using bio-signals.

The apparatus for determining a respiration state on the basis of a plurality of biological indicators calculated using bio-signals may include at least one processor and a memory configured to store instructions for instructing the at least one processor to perform at least one step.

The at least one step may include collecting a photoplethysmography (PPG) signal measured by a PPG sensor and a cutaneous electric signal measured by an electrodermal activity (EDA) sensor, analyzing the collected PPG signal and cutaneous electric signal and calculating a plurality of biological indicators including a respiration rate, and comprehensively evaluating the plurality of biological indicators to determine a user's respiration state.

The calculating of the plurality of biological indicators may include performing bandpass filtering on the PPG signal to extract a respiration signal and performing frequency analysis on the extracted respiration signal on a segment basis to calculate a respiration rate.

The performing of the frequency analysis to calculate the respiration rate may include determining an optimal size of sample data shared by continuous segments.

When the number of samples is N and the size of each segment is $\alpha \cdot N$, the optimal size ($\beta \cdot N$) of sample data may be determined to satisfy a relationship corresponding to the following equation:

$$\alpha \cdot N + x \cdot y = N$$

where, $y=(\alpha \cdot N)-(\beta \cdot \alpha \cdot N)$ $x=1/\alpha \cdot ((1-\alpha))/((1-\beta))$.

The plurality of biological indicators may further include a blood oxygen saturation and a cutaneous electric conductivity.

The PPG signal may be a signal that is acquired from reflected light with wavelengths of 660 nm and 940 nm.

The calculating of the plurality of biological indicators may include normalizing a 660-nm wavelength signal and a 940-nm wavelength signal of the PPG signal at a ratio of an alternating current signal to a direct current signal and calculating the blood oxygen saturation using a ratio between the normalized 660-nm wavelength signal and the normalized 940-nm wavelength signal.

The calculating of the blood oxygen saturation may include calculating the blood oxygen saturation to have a linear proportional relationship at the ratio between the normalized 660-nm wavelength signal and the normalized 940-nm wavelength signal.

The determining of the user's respiration state may include determining the respiration state as "normal respiration state" when the respiration rate falls within a normal threshold range, the blood oxygen saturation is greater than a minimal critical oxygen saturation, and the cutaneous electric conductivity is less than a neutral critical cutaneous conductivity.

The determining of the user's respiration state may include determining the respiration state as "abnormal physical or psychological state" when the respiration rate falls within a normal threshold range and the blood oxygen saturation is less than a minimal critical oxygen saturation or the cutaneous electric conductivity is greater than a neutral critical cutaneous conductivity.

The determining of the user's respiration state may include determining the respiration state as "dyspnea accompanied by oxygen deficiency symptoms due to hyperpnea" when the respiration rate is greater than a maximum value of a normal threshold range and the blood oxygen saturation is less than a minimal critical oxygen saturation.

The determining of the user's respiration state may include determining the respiration state as "dyspnea accompanied by a sticky skin symptom due to hyperpnea" when the respiration rate is greater than a maximum value of a normal threshold range and the cutaneous electric conductivity is greater than a neutral critical cutaneous conductivity.

The determining of the user's respiration state may include determining the respiration state as "urgent respiration state" when the respiration rate lies outside a normal threshold range, the blood oxygen saturation is less than a minimal critical oxygen saturation, and the cutaneous electric conductivity is greater than a neutral critical cutaneous conductivity.

In still other example embodiments, there is provided a method of calculating the number of breaths per minute using bio-signals.

The method of calculating the number of breaths per minute using bio-signals may include collecting a PPG signal measured by a PPG sensor, performing bandpass filtering on the PPG signal to extract a respiration signal, and performing frequency analysis on the extracted respiration signal on a segment basis to calculate a respiration rate.

BRIEF DESCRIPTION OF DRAWINGS

Example embodiments of the present invention will become more apparent by describing in detail example embodiments of the present invention with reference to the accompanying drawings, in which.

DETAILED DESCRIPTION OF EXAMPLE EMBODIMENTS

Figure 1:
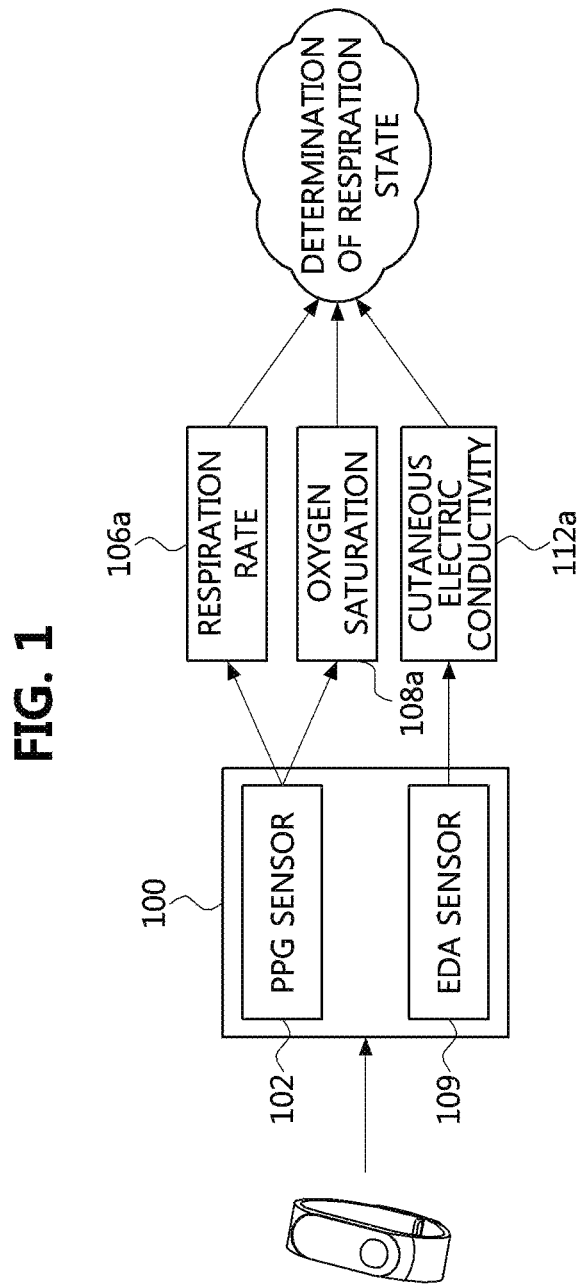
FIG. 1 is an example diagram illustrating a method of determining a respiration state on the basis of a plurality of biological indicators calculated using bio-signals according to an embodiment of the present invention.

Example embodiments of the present invention are disclosed herein. However, specific structural and functional details disclosed herein are merely representative for purposes of describing example embodiments of the present invention, and example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

FIG. 1 is an example diagram illustrating a method of determining a respiration state on the basis of a plurality of biological indicators calculated using bio-signals according to an embodiment of the present invention.

Referring to FIG. 1, the method of determining a respiration state according to an embodiment of the present invention may be performed by a wearable device 100 that can be easily worn by a user (hereinafter referred to as an apparatus for determining a respiration state on the basis of a plurality of biological indicators calculated using bio-signals). Here, the wearable device 100 may be embodied in the form of a band-type device that partially surrounds a user's head, wrist, face, or upper arm, a tongs-type device that grips the end or edge thereof, and an armband-type device that surrounds the entirety thereof. Also, the wearable device 100 may be adhered or coupled to various conventional mechanisms that can be worn by a user, such as a wrist watch or a wrist support.

Meanwhile, the wearable device 100 may include a photoplethysmography (PPG) sensor 102 and an electrodermal activity (EDA) sensor 109. Here, the PPG sensor 102 may be a sensor that may be built in one side of the wearable device 100 that is to be brought into contact with a user's body and that may be configured to emit light using a light emitting device (LED) and measure the user's pulse waves through reflected waves received from the body. In detail, the PPG sensor 102 may include a photoelectric device that emits light corresponding to a wavelength of 660 nm or 940 nm.

The EDA sensor 109 may be a sensor that senses changes in cutaneous electrical characteristics. Also, the EDA sensor 109 may be referred to as a sensor for sensing a human galvanic skin response (GSR).

The wearable device 100 according to an embodiment of the present invention may analyze a photoplethysmography (PPG) signal using the PPG sensor 102 to calculate a respiration rate (or a breathing rate) 106a and an oxygen saturation (or a respiration volume) 108a and may analyze an electrical signal of the skin measured by the EDA sensor 109 to calculate a cutaneous electric conductivity 112a.

Next, the wearable device 100 may comprehensively evaluate the respiration rate 106a, the oxygen saturation 108a, and the cutaneous electric conductivity 112a to determine a user's respiration state. In this case, the wearable device 100 may prioritize the respiration rate 106a and then evaluate a primary respiration state using the respiration rate 106a. By considering not only a result of the evaluation but also the oxygen saturation 108a and/or the cutaneous electric conductivity 112a, the wearable device 100 may evaluate a final respiration state. Alternatively, the wearable device 100 may evaluate the user's respiration state by weighting or comprehensively considering the respiration rate 106a, the oxygen saturation 108a, and the cutaneous electric conductivity 112a.

The term "respiration rate" used herein may refer to the number of breaths calculated per minute or per unit time and may be used interchangeably with the term "breathing rate."

The following description assumes that the wearable device 100 calculates a biological indicator and determines a respiration state, but the present invention is not limited thereto. For example, an external server or user terminal may receive bio-signals measured by the wearable device 100, calculate a biological indicator, and determine a respiration state.

Figure 2:
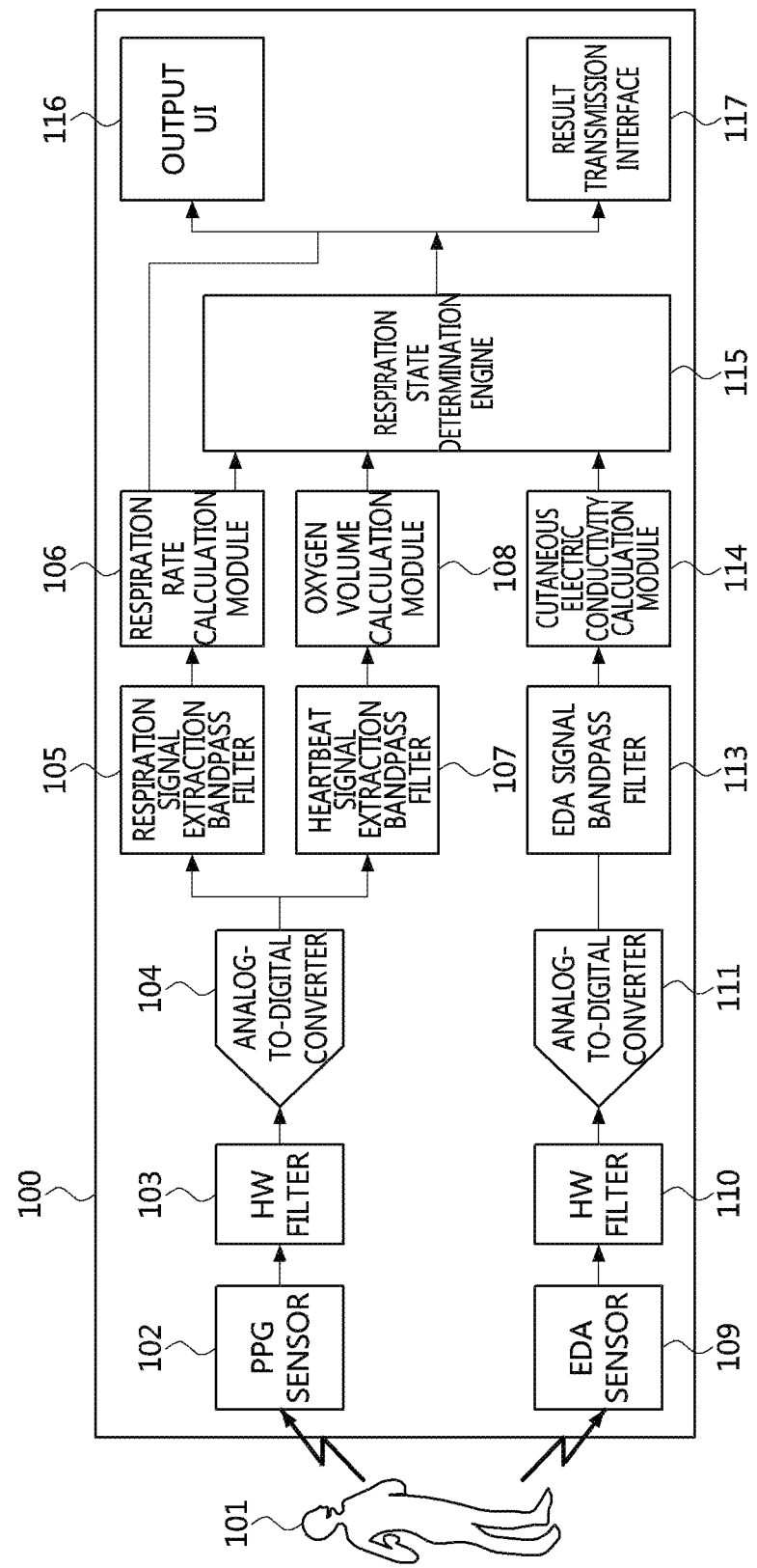
FIG. 2 is a block diagram showing a functional module of an apparatus for determining a respiration state on the basis of a plurality of biological indicators calculated using bio-signals according to an embodiment of the present invention.

FIG. 2 is a block diagram showing a functional module of an apparatus for determining a respiration state on the basis of a plurality of biological indicators calculated using bio-signals according to an embodiment of the present invention.

Referring to FIG. 2, functional sub-modules of an apparatus 100 for determining a respiration state on the basis of a plurality of biological indicators calculated using bio-signals, or the wearable device of FIG. 1 may be shown.

First, a PPG signal measured by the PPG sensor 102 may be filtered through a hardware (HW) filter 103 to remove signals unrelated to respiration or heartbeat (i.e., power signals, signal noise, or the like). In this case, the HW filter 103 is a filter for removing unnecessary signals and may be referred to as a bandstop filter. The signal filtered through the HW filter 103 may be converted into a digital signal through an analog-to-digital converter 104.

Only a frequency corresponding to a respiration signal may be extracted from the PPG signal converted into the digital signal, through a bandpass filter 105 for respiration signal extraction. A respiration rate calculation module 106 may analyze the respiration signal frequency extracted by the bandpass filter 105 for respiration signal extraction to calculate a respiration rate.

Alternatively, only a frequency corresponding to a heartbeat signal may be extracted from the PPG signal converted into the digital signal through a bandpass filter 107 for heartbeat signal extraction. An oxygen volume calculation module 108 may analyze the heartbeat signal frequency extracted by the bandpass filter 107 for heartbeat signal extraction to calculate a blood oxygen saturation.

Here, the bandpass filter 107 for heartbeat signal extraction and the bandpass filter 105 for respiration signal extraction are shown in the drawing, respectively, but may be implemented as a single functional module.

Meanwhile, a cutaneous electric signal measured by the EDA sensor 109 may be filtered through a HW filter 110 to remove signals unrelated to the cutaneous electric signal (i.e., power signals, signal noise, or the like). The signal filtered through the HW filter 110 may be converted into a digital signal through an analog-to-digital converter 111.

Only a frequency needed to measure the cutaneous electric conductivity may be extracted from the cutaneous electric signal converted into the digital signal, through a bandpass filter 113 for cutaneous electric conductivity measurement. Subsequently, a cutaneous electric conductivity calculation module 114 may analyze a cutaneous electric frequency extracted through the bandpass filter 113 to calculate a cutaneous electric conductivity.

A respiration state determination engine 115 may determine a respiration state of a subject in comprehensive consideration of biological indicators (the respiration rate, oxygen saturation, and cutaneous electric conductivity) calculated through the respiration rate calculation module 106, the oxygen volume calculation module 108, and the cutaneous electric conductivity calculation module 114.

The final respiration state and/or respiration rate determined by the respiration state determination engine 115 may be displayed to a user through a result output user interface (UI) 116 or a display unit or may be transmitted to an external server or a user terminal through an external result transmission communication interface 117 or a communication module.

Figure 3:
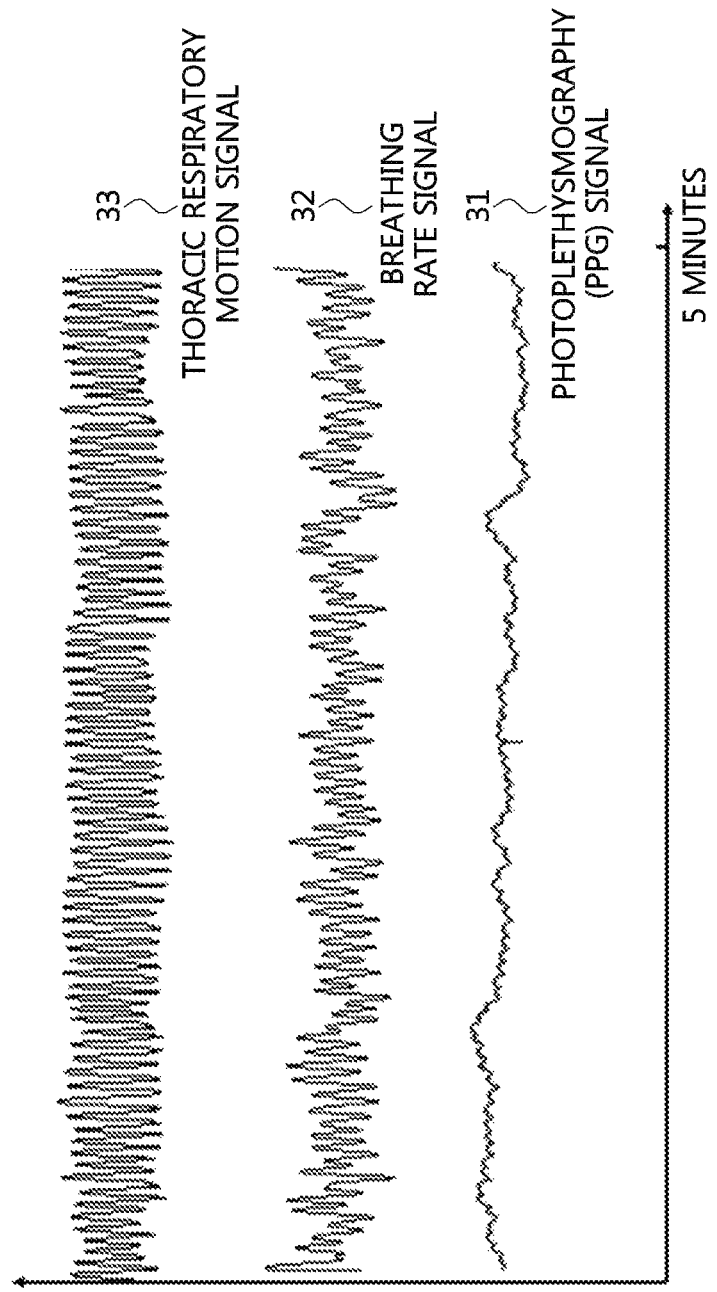
FIG. 3 is a graph in which a breathing rate signal and a respiratory motion signal are extracted through a photoplethysmography (PPG) signal.
Figure 4:
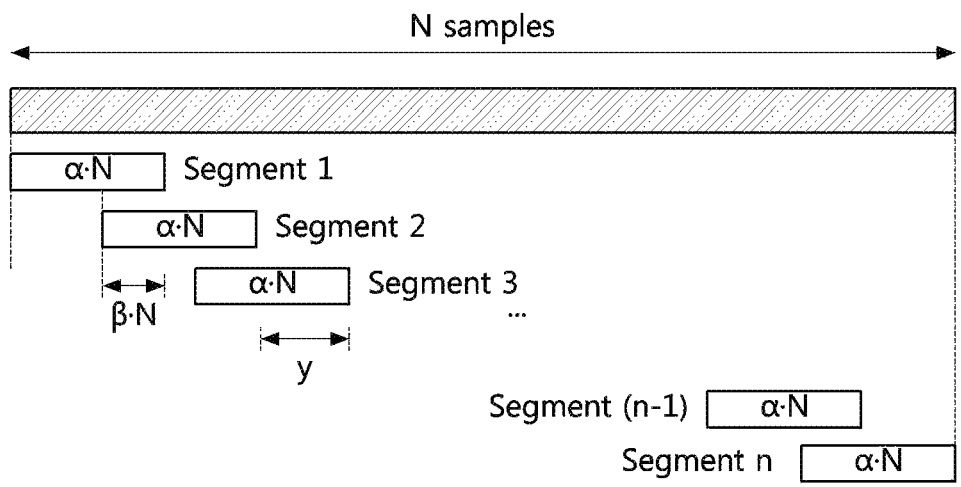
FIG. 4 is an example diagram illustrating a method of performing frequency analysis on a respiration signal on a segment basis.

FIG. 3 is a graph in which a breathing rate signal and a respiratory motion signal are extracted through a PPG signal. FIG. 4 is an example diagram illustrating a method of performing frequency analysis on a respiration signal on a segment basis.

Referring to FIG. 3, there is shown a graph obtained by comparing a respiratory motion signal of an actual chest measured using a commercial breath measuring system (BIOPAC Systems Inc., MP150, RESP100C) to a PPG signal 31 acquired through the PPG sensor and a respiration rate signal 32 calculated from the PPG signal 31.

First, a respiration signal may be extracted from the PPG signal 31 through the bandpass filter 105. In detail, the bandpass filter 105 of FIG. 2, which is for respiration signal extraction, may extract a respiration signal using Equation 1 below:

$$Y(t) = X(t)\sum_{k=0}^{N} b(k) \cdot z^{-k} + Y(t)\sum_{k=1}^{M} a(k) \cdot z^{-k} \qquad [\text{Equation 1}]$$

where X(t) may indicate a PPG signal converted into a digital signal, Y(t) may indicate an extracted respiration signal, and a(k) and b(k) may indicate bandpass filter coefficients.

Meanwhile, frequency analysis may be performed on the respiration signal calculated using Equation 1 on a segment basis. Referring to FIG. 4, N respiration signal samples are each divided into n segment units, and frequency analysis may be performed on each of the segment units.

The number of samples of each segment may be $\alpha \cdot N$ (here, N is the total number of samples, and $\alpha$ is a proportional constant), and continuous segments may share $\beta \cdot N$ overlapping samples. That is, $\beta \cdot N$ posterior samples of segment #1 may be used as initial samples of segment #2. By optimally determining the number of shared samples in this case, it is possible to more accurately perform frequency analysis.

For example, the number β·N of samples shared by continuous segments may be determined to have an optimal size through Equation 2 below:

$$\alpha \cdot N + x \cdot y = N$$

where, $y = (\alpha \cdot N) - (\beta \cdot \alpha \cdot N)$ $$x = 1/\alpha \cdot ((1-\alpha))/((1-\beta)).$$ [Equation 2]

By substituting values of x and y and the total number N of samples into Equation 2, it is possible to determine a relationship between a proportional constant α for a segment and a proportional constant β for the number of shared analysis samples. Also, on the basis of the relationship according to Equation 2, the number n of segments may be determined using Equation 3 below:

$$n = 1 + x.$$ [Equation 3]

Here, a variable x in Equation 3 may refer to Equation 2. That is, through the relationships of Equations 2 and 3, an optimal size of sample data shared by the continuous segments may be determined, and also the number of segments for frequency analysis may be determined.

Accordingly, a respiration rate may be calculated by analyzing respiration signals collected in real time on a segment basis according to FIG. 3 and Equation 2 by a first-in, first-out (FIFO) method. At this time, the respiration rate may be calculated by performing frequency conversion on each segment unit using the following Equation 4 and analyzing a respiration signal in the frequency domain.

$$Y(f) = \sum_{t=0}^{\frac{T}{2}-1} Y(2t)e^{-\frac{j2\pi(2t)f}{T}} + \sum_{t=0}^{\frac{T}{2}-1} Y(2t+1)e^{-\frac{j2\pi(2t+1)f}{T}}.$$ [Equation 4]

Referring to FIG. 4, there may be shown an equation for deriving a signal Y(f) obtained by transforming a respiration signal Y(t) into the frequency domain.

Referring to FIG. 3, there may be shown a signal indicating the calculated respiration rate over time. In this case, the number of breaths per minute may be determined as the breathing rate.

Figure 5:
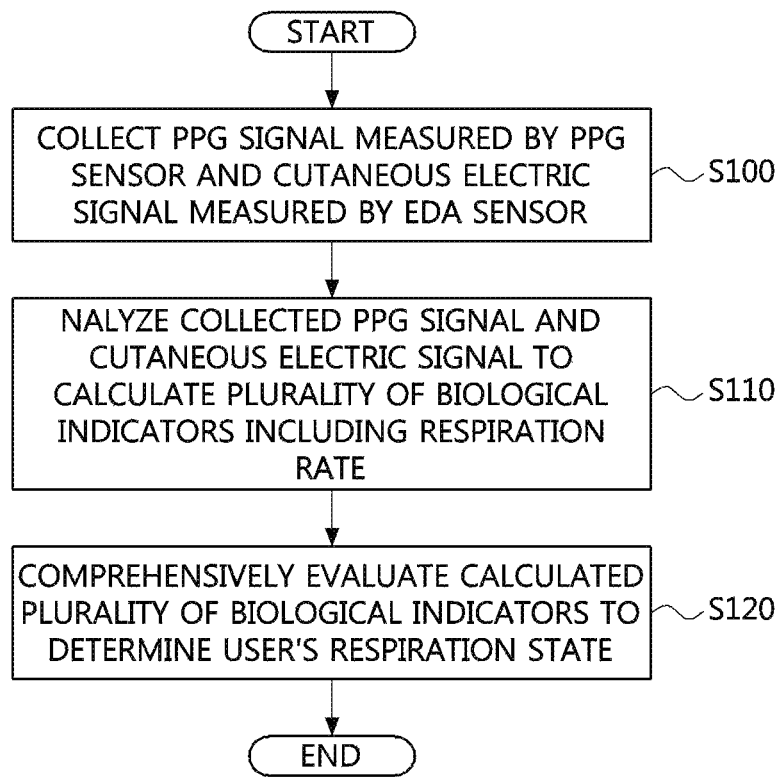
FIG. 5 is a flowchart showing a method of determining a respiration state on the basis of a plurality of biological indicators calculated using bio-signals according to an embodiment of the present invention.
Figure 6:
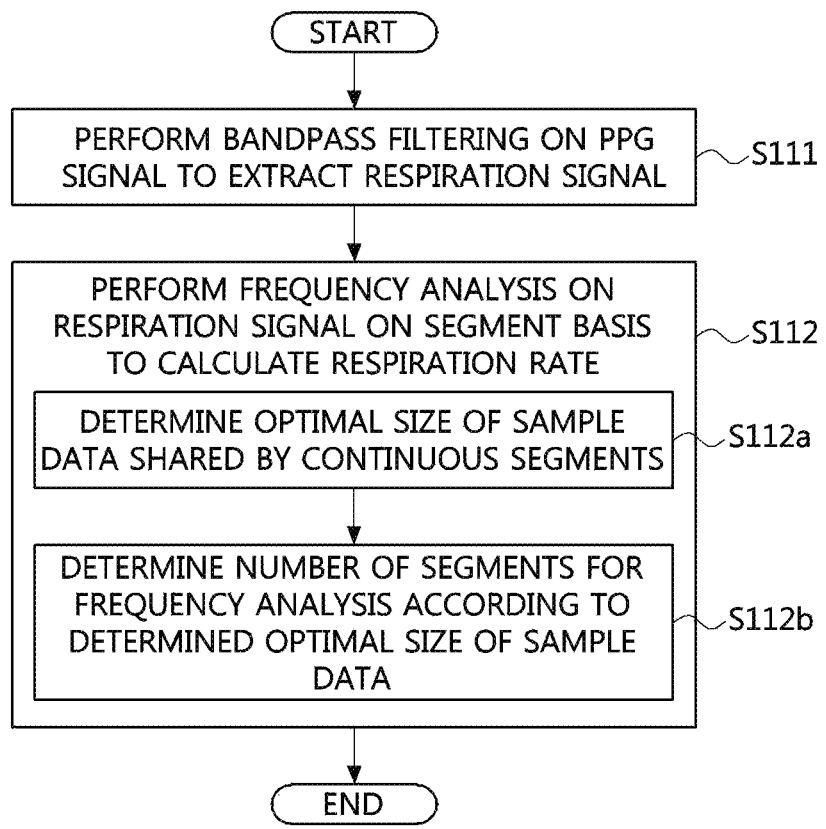
FIG. 6 is a flowchart illustrating a process of calculating a respiration rate according to an embodiment of the present invention.

FIG. 5 is a flowchart showing a method of determining a respiration state on the basis of a plurality of biological indicators calculated using bio-signals according to an embodiment of the present invention. FIG. 6 is a flowchart illustrating a process of calculating a breathing rate according to an embodiment of the present invention.

Referring to FIG. 5, the method of determining a respiration state on the basis of a plurality of biological indicators calculated using bio-signals may include collecting a PPG signal measured by a PPG sensor and a cutaneous electric signal measured by an EDA sensor (S100), analyzing the collected PPG signal and cutaneous electric signal and calculating a plurality of biological indicators including a respiration rate (S110), and comprehensively evaluating the plurality of biological indicators to determine a user's respiration state (S120).

In this case, referring to FIG. 6, the calculating of the plurality of biological indicators (S110) may include performing bandpass filtering on the PPG signal to extract a respiration signal (S111) and performing frequency analysis on the extracted respiration signal on a segment basis to calculate a respiration rate (S112).

The performing of the frequency analysis to calculate the respiration rate (S112) may include determining an optimal size of sample data shared by continuous segments (S112a).

Also, the performing of the frequency analysis to calculate the respiration rate (S112) may include determining the number of segments for frequency analysis according to the optimal sample data size (S112b).

Here, the optimal sample data size β·N may be determined to satisfy the relationship of Equation 2 when the number of samples is N and the size of each segment is α·N.

The plurality of biological indicators may further include a blood oxygen saturation and a cutaneous electric conductivity.

The blood oxygen saturation may be calculated using a signal obtained by a photoelectric device (or a light emitting diode) of the PPG sensor emitting light with wavelengths of 660 nm and 940 nm to a user's body part such as a wrist and reflecting the emitted light. That is, the PPG signal may be a signal that is acquired from the reflected light with wavelengths of 660 nm and 940 nm.

The blood oxygen saturation may be derived by calculating, from a signal with a wavelength of 660 nm, a normalized signal $RED_{norm}$ using a ratio of a direct current component $RED_{DC}$ and an alternating current component $RED_{AC}$, calculating, from a signal with a wavelength of 940 nm, a normalized signal $IR_{norm}$ using a ratio of a direct current component $IR_{DC}$ and an alternating current component $IR_{AC}$, and then calculating a ratio $PPG_{ratio}$ between the normalized signal $RED_{norm}$ with a wavelength of 660 nm and the normalized signal $IR_{norm}$ with a wavelength of 940 nm.

In detail, the ratio $PPG_{ratio}$ between the normalized signal $RED_{norm}$ with a wavelength of 660 nm and the normalized signal $IR_{norm}$ with a wavelength of 940 nm may be calculated using Equation 5 below:

$$PPG_{ratio} = \frac{RED_{norm}}{IR_{norm}} = \frac{\frac{RED_{AC}}{RED_{DC}}}{\frac{IR_{AC}}{IR_{DC}}}.$$ [Equation 5]

Also, the blood oxygen saturation may be determined using the ratio of Equation 5 to have a correlation (or a linear proportional relationship) of Equation 6 below:

$$SpO_2 = a + b \times PPG_{ratio}$$ [Equation 6]

Here, a and b are constants and may be empirically determined depending on a light emitting device and a region in which a user's blood oxygen saturation is measured.

In summary, the calculating of the plurality of biological indicators (S110) may include normalizing the 660-nm wavelength signal and the 940-nm wavelength signal of the PPG signal at the ratio of the alternating current component to the direct current component and calculating the blood oxygen saturation using the ratio between the normalized 660-nm wavelength signal and the normalized 940-nm wavelength signal.

The calculating of the blood oxygen saturation may include calculating the blood oxygen saturation to have a linear proportional relationship at the ratio between the normalized 660-nm wavelength signal and the normalized 940-nm wavelength signal.

According to another aspect of the present invention, there may be provided a method of calculating the number of breaths per minute using bio-signals.

The method of calculating the number of breaths per minute using bio-signals may include collecting a PPG signal measured by a PPG sensor, performing bandpass filtering on the PPG signal to extract a respiration signal, and performing frequency analysis on the extracted respiration signal on a segment basis to calculate a respiration rate.

In addition, a process that logically or conceptually coincides with those described in the specification may be included, and thus a detailed description thereof will be omitted in order to avoid redundant descriptions.

Figure 7:
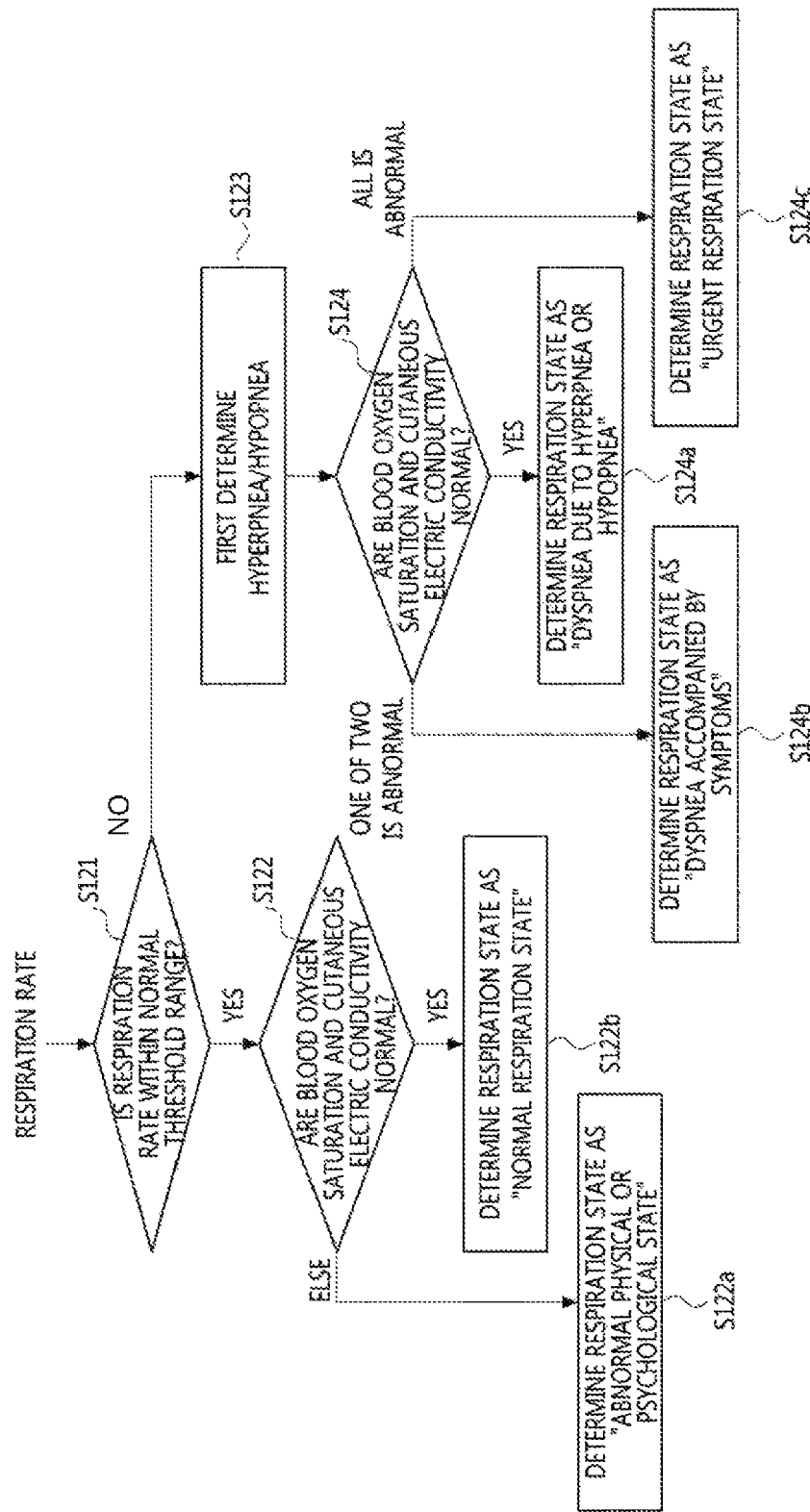
FIG. 7 is a flowchart illustrating a process of determining a respiration state on the basis of a plurality of biological indicators according to an embodiment of the present invention.

FIG. 7 is a flowchart illustrating a process of determining a respiration state on the basis of a plurality of biological indicators according to an embodiment of the present invention.

The determining of the user's respiration state according to FIG. 5 (S120) will be described in detail with reference to FIG. 7. In this case, a criterion for determining whether a blood oxygen saturation, a respiration rate, and a cutaneous electric conductivity are normal may be set as a determination criterion for determining the respiration state.

For example, whether the respiration rate is within a normal threshold range may be determined. When the respiration rate is greater than the maximum value of the normal threshold range, hyperpnea (or shallow breathing) may be determined. On the other hand, when the respiration rate is less than the minimum value of the normal threshold range, hypopnea (or deep breathing) may be determined.

Whether the blood oxygen saturation is greater than a predetermined minimal critical oxygen saturation may be determined. When the blood oxygen saturation is greater than the minimal critical oxygen saturation, it may be determined that the blood oxygen saturation is normal. On the other hand, when the blood oxygen saturation is less than the minimal critical oxygen saturation, it may be determined that the blood oxygen saturation is abnormal.

Also, whether the cutaneous electric conductivity is greater than a predetermined neutral critical cutaneous conductivity may be determined. In this case, the cutaneous electric conductivity may be determined to be normal when the cutaneous electric conductivity is greater than the neutral critical cutaneous conductivity and may be determined to be normal when the cutaneous electric conductivity is less than the neutral critical cutaneous conductivity.

Under these criteria, the process of determining the respiration state will be described with reference to FIG. 7.

First, whether the respiration rate calculated in S110 of FIG. 5 is within the normal threshold range may be determined (S121). When the respiration rate is within the normal threshold range, whether the blood oxygen saturation and the cutaneous electric conductivity are normal may be determined (S122).

When the determination result in S122 is that the blood oxygen saturation and the cutaneous electric conductivity are normal, the user's respiration state may be determined as "normal respiration state." In detail, when the respiration rate falls within the normal threshold range, the blood oxygen saturation is greater than the minimal critical oxygen saturation, and the cutaneous electric conductivity is less than the neutral critical cutaneous conductivity, the respiration state may be determined as "normal respiration state."

When the determination result in S122 is that at least one of the blood oxygen saturation and the cutaneous electric conductivity is abnormal, the user's respiration state may be determined as "abnormal physical or psychological state." In detail, when the respiration rate falls within the normal threshold range and the blood oxygen saturation is less than the minimal critical oxygen saturation or the cutaneous electric conductivity is greater than the neutral critical cutaneous conductivity, the respiration state may be determined as "abnormal physical or psychological state."

Meanwhile, when the determination result in S121 is that the respiration rate lies outside the normal threshold range, a primary respiration state of the user may be determined as hyperpnea or hypopnea (S123). In detail, the primary respiration state may be determined as hyperpnea when the respiration rate is greater than the maximum value of the normal threshold range and may be determined as hypopnea when the respiration rate is less than the minimum value of the normal threshold range.

After S123, whether the blood oxygen saturation and the cutaneous electric conductivity are normal may be determined (S124). When both of the blood oxygen saturation and the cutaneous electric conductivity are normal, the user's respiration state may be determined as "dyspnea due to hyperpnea or hypopnea" (S124a). That is, the user's respiration state may be determined as "dyspnea due to hyperpnea" in S124a when the first determination result in S123 is hyperpnea, and the user's respiration state may be determined as "dyspnea due to hypopnea" in S124a when the first determination result in S123 is hypopnea.

When any one of the blood oxygen saturation and the cutaneous electric conductivity is abnormal in S124, the user's respiration state may be determined as "dyspnea accompanied by symptoms" (S124b).

For example, when the first determination result in S123 is hyperpnea and the blood oxygen saturation is abnormal, the user's respiration state may be determined as "dyspnea accompanied by oxygen deficiency symptoms due to hyperpnea." In detail, when the respiration rate is greater than the maximum value of the normal threshold range and the blood oxygen saturation is less than the minimal critical oxygen saturation, the respiration state may be determined as "dyspnea accompanied by oxygen deficiency symptoms due to hyperpnea."

Also, when the first determination result in S123 is hyperpnea and the cutaneous electric conductivity is abnormal, the user's respiration state may be determined as "dyspnea accompanied by a sticky skin symptom due to hyperpnea." In detail, when the respiration rate is greater than the maximum value of the normal threshold range and the cutaneous electric conductivity is greater than the neutral critical cutaneous conductivity, the respiration state may be determined as "dyspnea accompanied by a sticky skin symptom due to hyperpnea."

In the same way as before, when the first determination result in S123 is hypopnea and the blood oxygen saturation is abnormal, the user's respiration state may be determined as "dyspnea accompanied by oxygen deficiency symptoms due to hypopnea." Also, when the first determination result in S123 is hypopnea and the cutaneous electric conductivity is abnormal, the user's respiration state may be determined as "dyspnea accompanied by a sticky skin symptom due to hypopnea."

When both of the blood oxygen saturation and the cutaneous electric conductivity are abnormal in S124, the user's respiration state may be determined as "urgent respiration state" (S124c). In detail, when the respiration rate lies outside the normal threshold range, the blood oxygen saturation is less than the minimal critical oxygen saturation, and the cutaneous electric conductivity is greater than the neutral critical cutaneous conductivity, the respiration state may be determined as "urgent respiration state."

Figure 8:
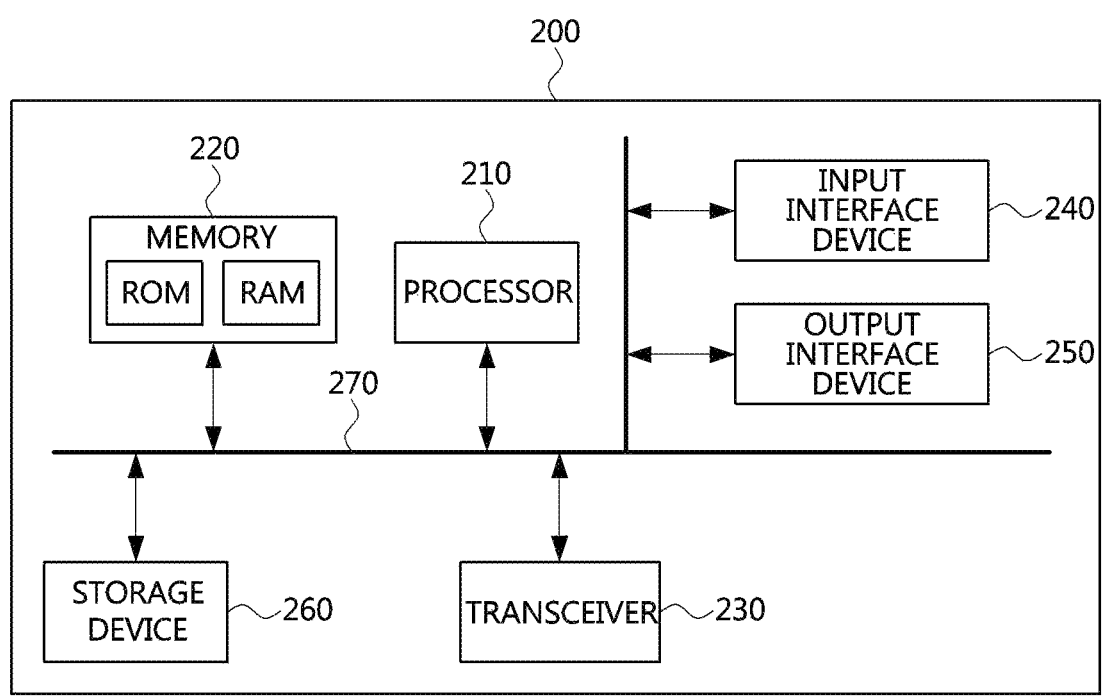
FIG. 8 is a hardware configuration diagram of an apparatus for determining a respiration state on the basis of a plurality of biological indicators calculated using bio-signals.

FIG. 8 is a hardware configuration diagram of an apparatus for determining a respiration state on the basis of a plurality of biological indicators calculated using bio-signals.

Referring to FIG. 8, an apparatus 200 for determining a respiration state on the basis of a plurality of biological indicators calculated using bio-signals may include at least one processor 210 and a memory 220 configured to store instructions for instructing the at least one processor 210 to perform at least one step.

The at least one processor 210 may refer to a central processing unit (CPU), a graphics processing unit (GPU), or a dedicated processor by which the methods according to embodiments of the present invention are performed. Each of the memory 220 and a storage device 260 may be composed of at least one of volatile and non-volatile storage media. For example, the memory 220 may be composed of at least one of a read only memory (ROM) and a random access memory (RAM).

Also, the apparatus 200 for determining a respiration state on the basis of a plurality of biological indicators calculated using bio-signals may include a transceiver 230 configured to perform communication over a wireless network. Also, the apparatus 200 for determining a respiration state on the basis of a plurality of biological indicators calculated using bio-signals may further include an input interface device 240, an output interface device 250, a storage device 260, and the like. Elements included in the apparatus 200 for determining a respiration state on the basis of a plurality of biological indicators calculated using bio-signals may be connected to, and communicate with, one another through a bus 270.

The at least one step may include collecting a PPG signal measured by a PPG sensor and a cutaneous electric signal measured by an EDA sensor, analyzing the collected PPG signal and cutaneous electric signal and calculating a plurality of biological indicators including a respiration rate, and comprehensively evaluating the plurality of biological indicators to determine a user's respiration state.

The calculating of the plurality of biological indicators may include performing bandpass filtering on the PPG signal to extract a respiration signal and performing frequency analysis on the extracted respiration signal on a segment basis to calculate a respiration rate.

The performing of the frequency analysis to calculate the respiration rate may include determining an optimal size of sample data shared by continuous segments.

The optimal sample data size $\beta \cdot N$ may be determined to satisfy the relationship of Equation 2 when the number of samples is N and the size of each segment is $\alpha \cdot N$.

The plurality of biological indicators may further include a blood oxygen saturation and a cutaneous electric conductivity.

The PPG signal may be a signal that is acquired from reflected light with wavelengths of 660 nm and 940 nm.

The calculating of the plurality of biological indicators may include normalizing a 660-nm wavelength signal and a 940-nm wavelength signal of the PPG signal at a ratio of an alternating current signal to a direct current signal and calculating the blood oxygen saturation using a ratio between the normalized 660-nm wavelength signal and the normalized 940-nm wavelength signal.

The calculating of the blood oxygen saturation may include calculating the blood oxygen saturation to have a linear proportional relationship with respect to the ratio between the normalized 660-nm wavelength signal and the normalized 940-nm wavelength signal.

The determining of the user's respiration state may include determining the respiration state as "normal respiration state" when the respiration rate falls within a normal threshold range, the blood oxygen saturation is greater than a minimal critical oxygen saturation, and the cutaneous electric conductivity is less than a neutral critical cutaneous conductivity.

The determining of the user's respiration state may include determining the respiration state as "abnormal physical or psychological state" when the respiration rate falls within a normal threshold range and the blood oxygen saturation is less than a minimal critical oxygen saturation or the cutaneous electric conductivity is greater than a neutral critical cutaneous conductivity.

The determining of the user's respiration state may include determining the respiration state as "dyspnea accompanied by oxygen deficiency symptoms due to hyperpnea" when the respiration rate is greater than a maximum value of a normal threshold range and the blood oxygen saturation is less than a minimal critical oxygen saturation.

The determining of the user's respiration state may include determining the respiration state as "dyspnea accompanied by a sticky skin symptom due to hyperpnea" when the respiration rate is greater than a maximum value of a normal threshold range and the cutaneous electric conductivity is greater than a neutral critical cutaneous conductivity.

The determining of the user's respiration state may include determining the respiration state as "urgent respiration state" when the respiration rate lies outside a normal threshold range, the blood oxygen saturation is less than a minimal critical oxygen saturation, and the cutaneous electric conductivity is greater than a neutral critical cutaneous conductivity.

The apparatus 200 for determining a respiration state on the basis of a plurality of biological indicators calculated using bio-signals may preferably be a wearable device, but may also be a desktop computer, a laptop computer, a notebook, a smartphone, a tablet PC, a mobile phone, a smart watch, smart glasses, an e-book reader, a portable multimedia player (PMP), a portable game machine, a navigation device, a digital camera, a digital multimedia broadcasting (DMB) player, a digital audio recorder, a digital audio player, a digital video recorder, a digital video player, a personal digital assistant (PDA), etc.

With the method and apparatus for determining a respiration state on the basis of a plurality of biological indicators calculated using bio-signals according to the present invention, it is possible to easily and precisely determine a respiration state using a wearable device.

Also, since complex indexes are used instead of simply a respiration rate, it is possible to detect a change in skin color or oxygen deficiency due to dyspnea and cope with the change.

While the example embodiments of the present invention and their advantages have been described in detail, it should be understood that various changes, substitutions and alterations may be made herein without departing from the scope of the invention.

What is claimed is:

1. A method of determining a respiration state on the basis of a plurality of biological indicators calculated using bio-signals, the method comprising:
    collecting a photoplethysmography (PPG) signal measured by a PPG sensor and a cutaneous electric signal measured by an electrodermal activity (EDA) sensor;

analyzing the collected PPG signal and the cutaneous electric signal and calculating a plurality of biological indicators including a respiration rate; and comprehensively evaluating the plurality of biological indicators to determine a user's respiration state, wherein the plurality of biological indicators further comprises a blood oxygen saturation and a cutaneous electric conductivity, wherein the determining of the user's respiration state comprises determining the respiration state as "normal respiration state" when the respiration rate falls within a predetermined threshold range, the blood oxygen saturation is greater than a minimal critical oxygen saturation, and the cutaneous electric conductivity is less than a predetermined neutral critical cutaneous conductivity.

2. The method of claim 1, wherein the calculating of the plurality of biological indicators comprises:

performing bandpass filtering on the PPG signal to extract a respiration signal; and performing frequency analysis on the extracted respiration signal on a segment basis to calculate a respiration rate.

3. The method of claim 2, wherein the performing of the frequency analysis to calculate the respiration rate comprises determining an optimal size of sample data shared by continuous segments.

4. The method of claim 3, wherein when a number of samples is N and a size of each segment is $\alpha \cdot N$, the optimal size ($\beta \cdot N$) of sample data is determined to satisfy a relationship corresponding to the following equation:

$$\alpha \cdot N + x \cdot y = N$$

where, $y = (\alpha \cdot N) - (\beta \cdot \alpha \cdot N)$ $$x = 1/\alpha \cdot ((1-\alpha))/((1-\beta)).$$

5. The method of claim 1, wherein the PPG signal is a signal obtained by light with wavelengths of 660 nm and 940 nm being reflected.

6. The method of claim 5, wherein the calculating of the plurality of biological indicators comprises:

normalizing a 660-nm wavelength signal and a 940-nm wavelength signal of the PPG signal at a ratio of an alternating current signal to a direct current signal; and calculating the blood oxygen saturation using a ratio between the normalized 660-nm wavelength signal and the normalized 940-nm wavelength signal.

7. The method of claim 1, wherein the determining of the user's respiration state comprises determining the respiration state as "abnormal physical or psychological state" when the respiration rate falls within the predetermined threshold range and the blood oxygen saturation is less than a minimal critical oxygen saturation or the cutaneous electric conductivity is greater than the predetermined neutral critical cutaneous conductivity.

8. The method of claim 1, wherein the determining of the user's respiration state comprises determining the respiration state as "dyspnea accompanied by oxygen deficiency symptoms due to hyperpnea" when the respiration rate is greater than a maximum value of the predetermined threshold range and the blood oxygen saturation is less than a minimal critical oxygen saturation.

9. The method of claim 1, wherein the determining of the user's respiration state comprises determining the respiration state as "dyspnea accompanied by a sticky skin symptom due to hyperpnea" when the respiration rate is greater than a maximum value of the predetermined threshold range and the cutaneous electric conductivity is greater than the predetermined neutral critical cutaneous conductivity.

10. The method of claim 1, wherein the determining of the user's respiration state comprises determining the respiration state as "urgent respiration state" when the respiration rate lies outside the predetermined threshold range, the blood oxygen saturation is less than a minimal critical oxygen saturation, and the cutaneous electric conductivity is greater than the predetermined neutral critical cutaneous conductivity.

11. An apparatus for determining a respiration state on the basis of a plurality of biological indicators calculated using bio-signals, the apparatus comprising:

at least one processor; and a memory configured to store instructions for instructing the at least one processor to:

collect a photoplethysmography (PPG) signal measured by a PPG sensor and a cutaneous electric signal measured by an electrodermal activity (EDA) sensor;

analyze the collected PPG signal and cutaneous electric signal and calculate a plurality of biological indicators including a respiration rate; and comprehensively evaluate the plurality of biological indicators to determine a user's respiration state, wherein the plurality of biological indicators further comprises a blood oxygen saturation and a cutaneous electric conductivity, wherein the instructions for instructing the at least one processor to comprehensively evaluate the plurality of biological indicators to determine the user's respiration state comprise instructions for instructing the at least one processor to determine the respiration state as "normal respiration state" when the respiration rate falls within a predetermined threshold range, the blood oxygen saturation is greater than a minimal critical oxygen saturation, and the cutaneous electric conductivity is less than a predetermined neutral critical cutaneous conductivity.

12. The apparatus of claim 11, wherein the instructions for instructing the at least one processor to calculate the plurality of biological indicators comprise instructions for instructing the at least one processor to:

perform bandpass filtering on the PPG signal to extract a respiration signal; and perform frequency analysis on the extracted respiration signal on a segment basis to calculate a respiration rate.

13. The apparatus of claim 12, wherein the instructions for instructing the at least one processor to perform the frequency analysis to calculate the respiration rate comprise instructions for instructing the at least one processor to determine an optimal size of sample data shared by continuous segments.

14. The apparatus of claim 13, wherein when a number of samples is N and a size of each segment is $\alpha \cdot N$, the optimal size ($\beta \cdot N$) of sample data is determined to satisfy a relationship corresponding to the following equation:

$$\alpha \cdot N + x \cdot y = N$$

where, $y = (\alpha \cdot N) - (\beta \cdot \alpha \cdot N)$ $$x = 1/\alpha \cdot ((1-\alpha))/((1-\beta)).$$

15. The apparatus of claim 11, wherein the instructions for instructing the at least one processor to determine the user's respiration state comprises instructions for instructing the at least one processor to determine the respiration state as "abnormal physical or psychological state" when the respiration rate falls within the predetermined threshold range and the blood oxygen saturation is less than a minimal critical oxygen saturation or the cutaneous electric conductivity is greater than the predetermined neutral critical cutaneous conductivity.

16. A method of calculating a number of breaths per minute using bio-signals, the method comprising:
- collecting a photoplethysmography (PPG) signal measured by a PPG sensor;
- performing bandpass filtering on the PPG signal to extract a respiration signal;
- acquiring a blood oxygen saturation and a cutaneous electric conductivity;
- performing frequency analysis on the extracted respiration signal on a segment basis to calculate a respiration rate; and
- determining a user's respiration state as "normal respiration state" when the respiration rate falls within a predetermined threshold range, the blood oxygen saturation is greater than a minimal critical oxygen saturation, and the cutaneous electric conductivity is less than a predetermined neutral critical cutaneous conductivity.

* * * * *